United States Patent [19]
Broerman

[11] Patent Number: 5,601,115
[45] Date of Patent: Feb. 11, 1997

[54] MULTIPORT SAMPLING VALVE

[75] Inventor: Arthur B. Broerman, Bartlesville, Okla.

[73] Assignee: Vantege Technologies, Inc., North Branch, N.J.

[21] Appl. No.: 454,681

[22] Filed: May 31, 1995

[51] Int. Cl.$^6$ .................................................. F16K 11/10
[52] U.S. Cl. ........................ 137/595; 137/597; 137/625.11
[58] Field of Search .......................... 137/625.11, 625.18, 137/595, 597

[56] References Cited

U.S. PATENT DOCUMENTS

| | | | |
|---|---|---|---|
| 2,575,240 | 11/1951 | Thompson | 137/144 |
| 2,911,008 | 11/1959 | Du Bois | 137/625.31 |
| 2,964,938 | 12/1960 | Fuller | 73/23 |
| 3,111,849 | 11/1963 | Broerman | 73/422 |
| 3,139,755 | 7/1964 | Reinecke et al. | 73/422 |
| 3,140,615 | 7/1964 | Broerman | 73/422 |
| 3,198,018 | 8/1965 | Broerman | 73/422 |
| 3,223,123 | 12/1965 | Young | 137/625.46 |
| 3,376,894 | 4/1968 | Broerman | 137/625.48 |
| 3,387,496 | 6/1968 | Broerman | 73/422 |
| 3,417,605 | 12/1968 | Hahn | 73/23 |
| 3,439,542 | 4/1969 | McCray | 73/422 |
| 3,492,873 | 2/1970 | Broerman et al. | 73/422 |
| 3,535,939 | 10/1970 | Casey et al. | 73/422 |
| 3,545,491 | 12/1970 | Broerman | 137/625.68 |
| 3,633,426 | 1/1972 | Broerman | 73/422 |
| 4,112,766 | 9/1978 | Ragains | 73/422 |
| 4,276,907 | 7/1981 | Broerman | 137/637.2 |
| 5,193,581 | 3/1993 | Shiroto et al. | 137/625.11 |

Primary Examiner—John C. Fox
Attorney, Agent, or Firm—Roper & Quigg

[57] ABSTRACT

A multiport, diaphragm-sealed valve suitable for use in sampling systems. Using a rotational movement, which can be electrically controlled, the valve operates without leakage or intermingling of transfer fluids to provide a simultaneous seal of all fluid pathways during the switching of flowpaths. multiport, diaphragm-sealed valve suitable for use in sampling systems. Using a rotational movement, which can be electrically controlled, the valve operates without leakage or intermingling of transfer fluids to provide a simultaneous seal of all fluid pathways during the switching of flow paths.

19 Claims, 3 Drawing Sheets

MULTIPORT SAMPLING VALVE

BACKGROUND OF THE INVENTION

1. Field of the Invention.

This invention relates to a multiport, diaphragm-sealed valve mechanism. In one of its aspects it relates to a motor-actuated, multi-position, sampling valve suitable for use with general process and analytical systems. In a more specific aspect of the invention it relates to a multiport valve with a uniform action mechanism for simultaneously sealing all transfer passages as the channels of flow are repositioned. In another of its aspects it relates to a method for transferring fluid samples and purge fluids through analyzer systems. In yet another of its aspects it relates to a method for manipulating the transfer of multiple fluids through a multiport valve mechanism with leakage and intermingling of transfer fluids minimized to the point of elimination.

2. Description of the Present State of the Field of the Invention

In a series of prior United States patents of which A. B. Broerman is an inventor—U.S. Pat. No. 3,111,849, 3,198,018, 3,140,615, 3,376,894, 3,387,496, 3,492,873, 3,545,491, 3,533,426 and 4,276,907—all incorporated herein by reference, various apparatuses have been set forth relating to multiport valve mechanisms particularly for use with chromatographic analyzers. In this series of patents the use of fluid piston operation to activate the valves is explored along with various means for sealing the fluid transfer pathways within the valve. In general, the actuation of the valves used in current practice depends on the use of individual electrical signals to switch individual solenoids to air power to actuate individual valve operators thereby causing use of a complex and, therefore, expensive multiplicity of solenoids in the valve operation and also provides an increased opportunity for fluid leaks and intermingling of transfer fluids. None of the prior art sets forth apparatus incorporating instantly actuated operation of the valves and uniform action, positive, simultaneous sealing of the flow paths as the paths are switched from one to another.

It is therefore an object of this invention to provide a rotary valve apparatus and method of operation that instantly switches the paths of flow within the valve. It is another object of this invention to provide valve apparatus and method of operation that simultaneously produces a positive seal of all the fluid pathways within the valve as the flow in the pathways is switched from one to another. It is another object of the invention to provide a sampling and column switching valve for use with analytical and other process systems which minimizes leaks and intermingling of fluids to the point of elimination. Still another object of the invention is to provide a valve for use with analytical systems which combines the functions of sampling and column switching in a single unit which is electrically actuated instantaneously and operates without leakage or intermingling of the transfer fluids. A specific object is to provide a valve with a twelve port configuration according to this invention.

These and other aspects and objects of the invention will become apparent on studying the following specification and claims along with the appended drawings.

SUMMARY OF THE INVENTION

According to this invention there is provided a multiport valve which has (A) a plunger body having a first, flat face and a second, flat face, (B) a detent plate; (C) a flat surface abutting the first, flat face of the plunger body and (D) at least one diaphragm inserted between the first, flat face of the plunger body and the surface abutting the first, flat face of the plunger body covering the area therebetween. The first, flat face of the plunger body has at least one, circular groove with the at least one groove pierced at equidistant intervals by a multiplicity of plunger passages with each, plunger passage (a) passing through the plunger body to the opposing, second, flat face, (b) retaining therein a plunger and (c) retaining partially therein a spherical body. The surface abutting the grooved, first, flat face of the plunger body includes transport tubing openings aligned at intervals in at least one, circular pattern concentric with and having the same diameter as an at least one, circular groove of the plunger body and with openings aligned between the plunger passages of the plunger body. The detent plate (a) has a flat face having indentions therein aligned at intervals in at least one, circular pattern concentric with and having the same diameter as the at least one, circular groove; (b) is held in position with the flat face of the detent plate facing the second, flat face of the plunger body so that the flat face of the detent plate holds each spherical body in sufficient, rollable tension in a retaining, plunger passage against a plunger to seal the diaphragm at the opposing end of the plunger against the surface abutting the grooved, first, flat face of the plunger body; and (c) is rotatable around an axis designated by a line joining the centers of the circles described by the at least one, circular groove and the at least one, circular pattern of indentations so that on partial rotation of the detent plate the spherical bodies providing tension on a portion of the plungers in the same groove simultaneously come to rest in indentations thereby allowing relaxation of the sealing of the diaphragm by these plungers against the abutting surface.

Also, according to this invention, there is provided a method for operating a multiport valve of this invention to provide combined sampling and column switching for operation of analytical and other processes by directing flow through specific paths for automatically-controlled periods of time.

In a specific embodiment, used to illustrate this invention, there is provided, with method of operation, a multiport valve which has twelve, transport tubing openings in equal spacing in two, concentric, circular patterns each having six openings aligned with the two grooves on the first face of the plunger body and with each groove providing entrance to six, equally-spaced, plunger passages. The detent plate has two, concentric, circular patterns of three indentations spaced at 120° intervals aligned with the concentric grooves on the plunger body. The detent plate is rotated in 60° movements which during the period in which none of the spherical bodies are aligned with the indentations in the detent plate causes sealing of all of the passages between transport tubing openings. On alignment of a spherical body with an indentation in the detent plate, the seal corresponding to that position is relaxed so that a path can be formed for fluid issuing from one of the transport tubing openings through the groove to the adjacent transport tubing opening.

DESCRIPTION OF THE PREFERRED EMBODIMENT

Figure 1:
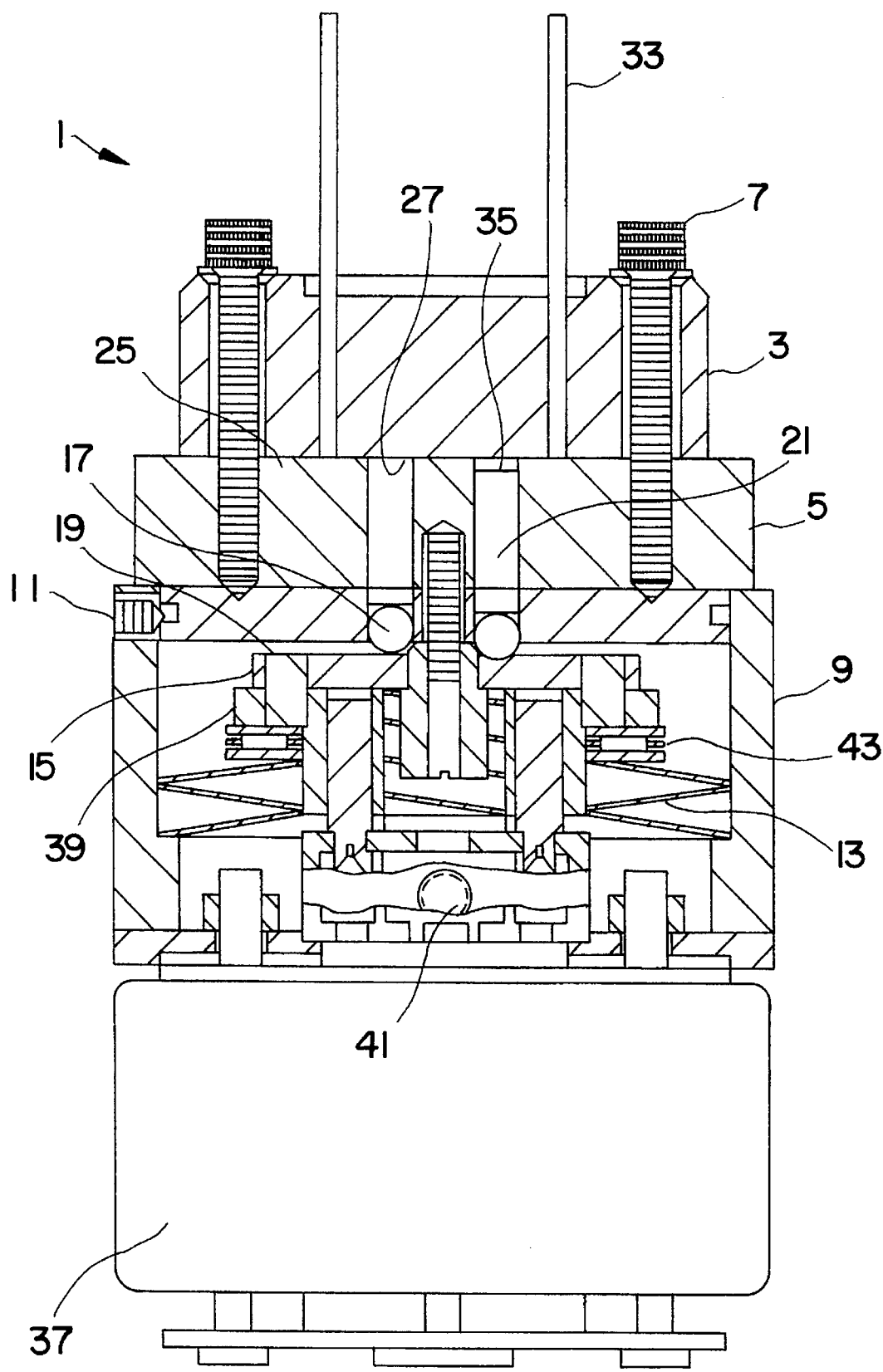
FIG. 1 is a view, shown partially in section, of a valve of this invention with a rotating mechanism attached thereto.
Figure 2:
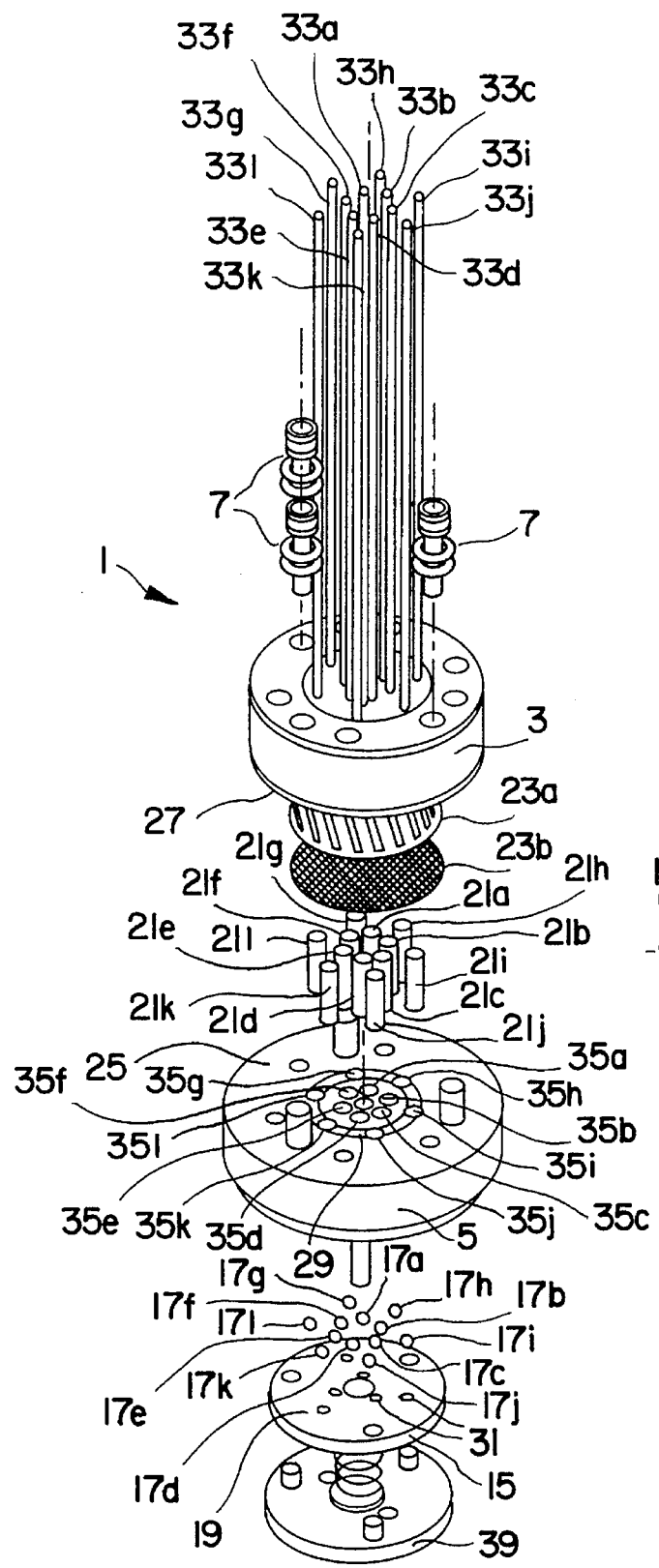
FIG. 2 and FIG. 3 are, in continuation, an exploded, perspective view, partially in section, of a valve of this invention with a rotating mechanism attached thereto.
Figure 3:
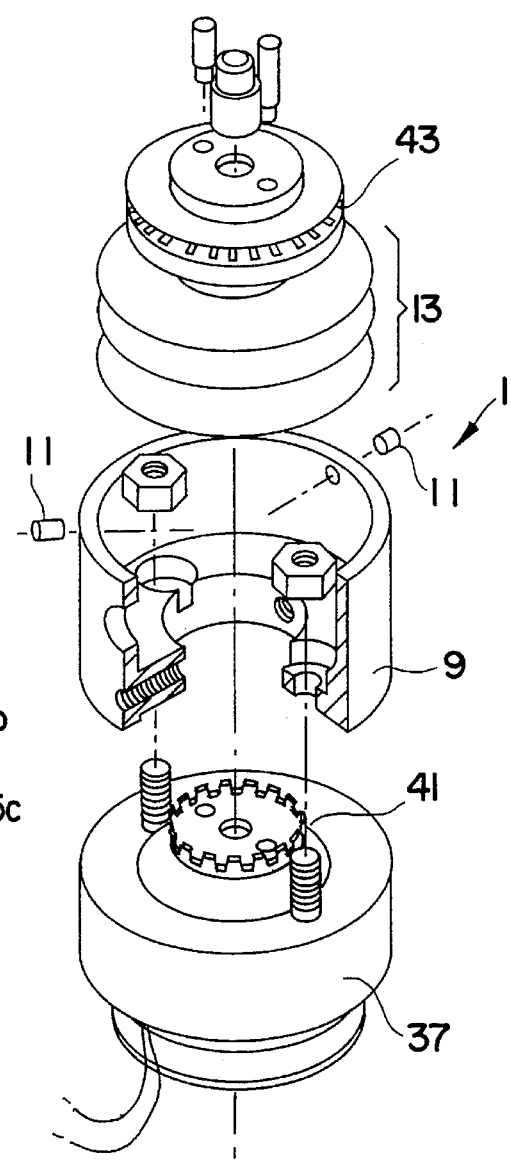

Referring to the drawing, particularly to FIGS. 1–3, the mechanism of a multiport valve of this invention and its operation will be described generally and in detail using a twelve port valve as illustration. Using a twelve port valve for the illustration is important because a valve with this number of ports has advantages over other known valves with lesser number of ports: (1) twelve ports in one valve is, in essence, constructing two six port valves in one frame thereby saving material of construction and operating space, (2) the inner and outer rings of ports can be linked to perform a greater number of functions, (3) the reduced "dead volume" between ports in the inner ring of ports provides increased efficiency in such services as sampling for high resolution chromatography and (4) the double ring valve is highly efficient in switching speed.

Referring to FIGS. 1 and 2, fluids, which can be either gases or liquids, are directed into and out of multiport valve 1 through a valve cap 3 which is fastened to a plunger body 5 by means such as a capscrew 7.

Referring to FIGS. 1, 2 and 3, the plunger body 5 is in turn attached to a casing 9 by means such as assembly screw 11 so that spring nest 13 is supported and acts to provide compression of the detent plate 15 against the spherical bodies 17 that are held in rolling abutment with both the face of the detent plate 19 and the plungers 21 to press the plungers against a diaphragm 23 inserted between the plunger body face 25 and the flat surface of the valve cap face 27 thereby sealing the diaphragm 23 to the valve cap face 27.

The diaphragm 23 is preferably two separate objects-(1) the sealing diaphragm 23a which is placed adjacent the flat surface of the valve cap face 27 and is composed of an impermeable film of a polymeric plastic that is chemically inert and heat resistant, preferably polytetrafluoroethylene and (2) the supporting diaphragm 23b which is placed between the sealing diaphragm 23a and the plunger body face 25 and is composed of a fabric of heat resistant polymer fiber, preferably a polyamine fiber, more preferably a polyaramid fiber such as Nomex, a trademark of E. I. Du Pont de Nemours & Co. The sealing diaphragm 23a must be of sufficient size to cover the circular grooves 29 on the plunger body face 25. The supporting diaphragm 23b has at least the diameter of the sealing diaphragm and is preferably the same diameter.

The sealing diaphragm provides the seal and the supporting diaphragm helps to prevent both cold flowing and ballooning of the sealing diaphragm under the alternating pressures encountered. The supporting diaphragm tends to minimize variations in the thickness of the sealing diaphragm by distributing the pressure on the sealing diaphragm against the plunger body face 25.

Essential to the operation of the invention, as will be shown, are (a) a circular groove or concentric, circular grooves 29 in the plunger body face 25 in circular alignment with openings of the fluid transport tubes 33 in the flat surface of the valve cap face 27; (b) the equidistant spacing of plunger passages 35 in these circular grooves 29, offset to be aligned between the transport tube openings, with the passages passing through the plunger body 5 thereby providing alignment of the plungers 21 retained therein and the spherical bodies 17 partially retained therein in rolling abutment with the face of detent plate 19; (c) the alignment of the indentations in the detent plate to receive a portion of the spherical bodies and (d) a diaphragm sufficiently resilient to be deformed into a groove but also sufficiently sturdy to withstand the varying pressures of the operation of the valve.

The face of the detent plate 19 and the spherical bodies 17 are made of a material that is highly resistant to wear. Various grades of alloy steel and carbides are suitable. A refractory carbide is the preferred material for constructing these items.

The valve cap 3 is attachable to the plunger body 5 at the first, flat face of the plunger body 25 and comprises (1) a valve cap body, (2) the surface abutting the first, flat face of the plunger body and (3) a multiplicity of transport tubings 33a–l press fitted into and through the valve cap body and machine lapped to the surface abutting the first, flat face of the plunger body forming thereby means of entrance and exit for fluid.

The operation of the valve is carried out by rotating the detent plate 15 around an axis, defined as the line connecting the centers of the circles described by the grooves, transport tubing openings and plunger passages, so that the rotation is stopped when indentations 31 in circular alignment with the circular grooves 29 and equidistantly spaced on the circular alignment are brought into contact with a portion of the spherical bodies 17 thereby allowing these spherical bodies to settle into the indentations sufficiently that the pressure of fluid entering the space between the flat surface of the valve cap face 27 abutting the grooved, first, flat face of the plunger body and the diaphragm 23 pushes the diaphragm to deform into the groove 29 thereby forming a path for the fluid from one transport tubing opening across the top of the diaphragms pushing the plunger into the plunger passage 35, and on to a transport tubing opening adjacent to the entry opening.

This operation is easily understood viewing the twelve port valve illustrated in the drawing at FIGS. 2 and 3. Assume that the valve has been in operation so that alternate spherical bodies 17a, 17c, 17e, 17g, 17i, 17k are resting in detent plate indentations 31. Spherical bodies 17b, 17d, 17f, 17h, 17j, 17l are pressed by the detent plate 15 against one end of plungers 21b, 21d, 21f, 21h, 21j, 21l sealing the other end of these plungers against the diaphragm 23 and at points between the transport tubing openings effectively sealing the diaphragm against the flat surface of the valve cap face 27 abutting the grooved, first, flat face of the plunger body thereby sealing the groove against passage of fluid at these points.

The detent plate 15 is then rotated 60°. As the detent plate rotates, none of the spherical bodies are aligned with detent plate indentations so that all of the plungers are pressured against the diaphragm and there is an effective sealing at points between every transport tubing opening against the passing of fluid through the groove. When the 60° rotation is completed, alternate spherical bodies 17b, 17d, 17f, 17h, 17j, 17l are resting in detent plate indentations 31. Spherical bodies 17a, 17c, 17e, 17g, 17i, 17k are pressed by the detent plate 15 against one end of plungers 21a, 21c, 21e, 21g, 21i, 21j sealing the other end of these plungers against the diaphragm 23 and at points between the transport tubing openings effectively sealing the diaphragm against the flat surface of the valve cap face 27. Between the points at which the pathway is now sealed, pressure of fluid from one of the transport tubing openings pushes the diaphragm into the groove from that opening across the plungers 21b, 21d, 21f, 21h, 21j, 21l to the opening having lower pressure thereby establishing a path of flow.

Using the twelve port model, every 60° rotation of the detent plate closes one set of pathways through the valve and opens another. At 120° rotation of the detent plate the previous pathways are opened so that the continuing forward rotation of the detent plate alternates the opening of the pathways. Operation with one forward rotation of 60° followed by one 60° rotation backward is also possible but obviously will not distribute wear on the detent plate as evenly as continuous forward rotation.

It is apparent that adjustment of the number of indentations on the detent plate in accordance with the number of pairs of transport tubes desired for use can provide versatility and easy adaptation of the twelve Fort apparatus described above to other even numbers of transport tubes that are a multiple of three or four. For instance, two indentations in a detent plate with a rotation of 90° will serve four ports in a single groove; four indentations in a detent plate with a rotation of 45° will serve eight ports in a single groove; for sixteen ports use two grooves of eight ports with two circles of four indentations and rotation of 45° or as an alternative for twelve ports use three grooves of four ports with three circles of two indentations with rotation of 90°. The limit is the practicality of using a large number of ports in a single valve structure.

Rotation of the detent plate can be supplied by commercially available rotary electric solenoids such as a Ledex rotary solenoid available from Lucas Ledex, Vandalia, Ohio. In this type of solenoid the stator contains (1) an electrically actuated coil and (2) magnetic inductance metal in a rotary member. On an electrical pulse the stator and the material in the rotor are magnetized to a strong mutual attraction. This causes rotation of the rotor around the stator which can be limited to a fixed number of degrees.

Figure 4:
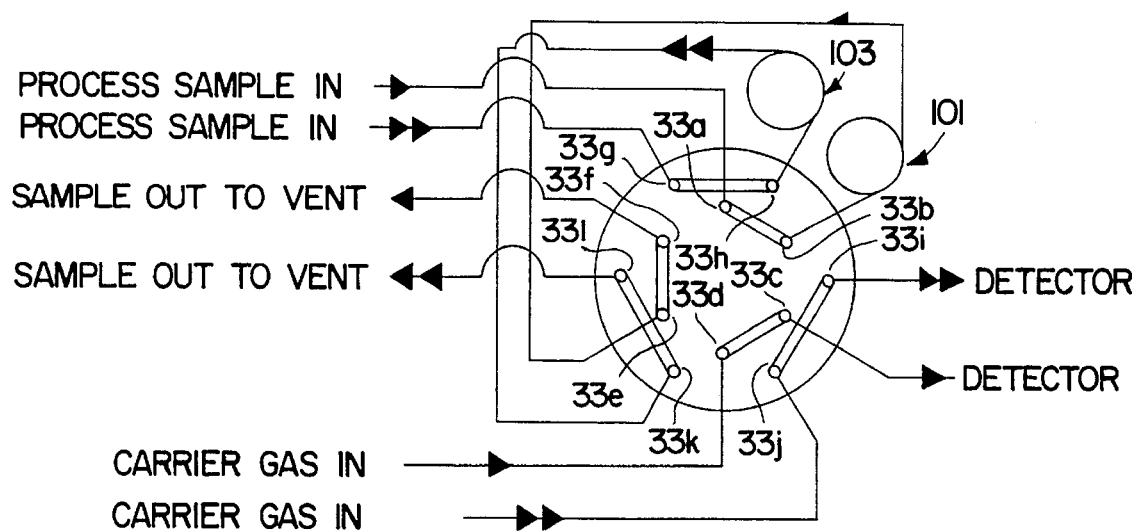
FIG. 4 is a schematic representation of the flow paths between ports of the twelve port valve during mode I of operation.

As shown in FIGS. 3 and 4 a rachet which is part of the solenoid 37 interacts with a ratchet assembly 41 which has rods interlocking into rotor driver 39 which rotates the detent plate 15. Positive stops built into the rotary solenoid determine the number of degrees of arc the rotor can move.

The solenoid is attached to the casing 9 of the spring nest 13. The solenoid and the spring nest, preferably spring washers, do not move. The rotation of the rotor driver is allowed by positioning a needle thrust bearing 43 between the spring nest 13, held in position in the casing 9, and the rotor driver 39. The hold down for the detent plate 15 prevents this plate from moving out of alignment with the plunger body 5.

Figure 5:
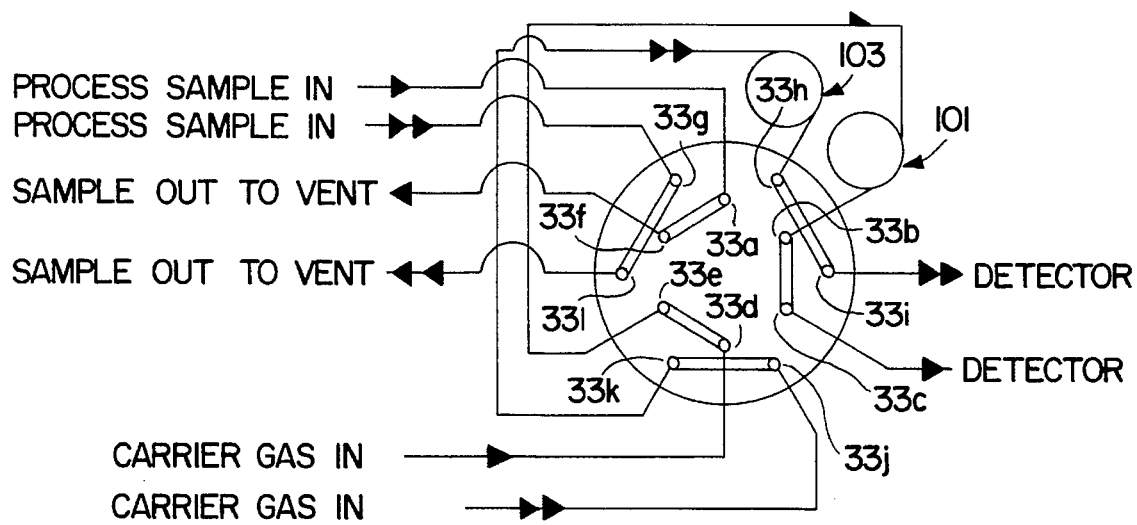
FIG. 5 is a schematic representation of the flow paths between ports of the twelve port valve during mode II of operation.

Referring now to FIGS. 4 and 5, operation of a chromatographic analyzing system using a twelve port valve made according to this invention will be described. This valve has six outlet ports for transport tubings 33a–f in an inner circular alignment and six outlet ports for transport tubings 33g–l in an outer circular alignment. Tubings 33b and 33e are permanently connected to an external sample loop 101 and tubings 33h and 33k are permanently connected by an external sample loop 103.

Referring now to FIGS. 2, 4 and 5, in mode I spherical bodies 17a, 17c, 17e, 17g, 17i and 17k are resting in the indentations 31 in the detent plate 15 and the compressive pressure of spherical bodies 17b, 17d, 17f, 17h, 17j and 17l, transmitting the pressure of the springs 13 against the detent plate 15, through the plungers 21 press the diaphragm 23 against the flat surface of the valve cap face 27 thereby blocking passage of fluid through the grooves between alternate pairs of ports for transfer tubings 33b–33c, 33d–33e, 33f–33g, 33h–33i, 33j–33k and 33l–33g and allowing the diaphragm 23 to be deformed into portions of the grooves 29 by fluid entering the grooves from the ports providing a fluid flow path between ports for transfer tubings 33a–33b, 33c–33d, 33e–33f, 33g–33h, 33i–33j and 33k–33l.

In mode I, as indicated in FIG. 4, in the inner circle of ports a continuously flowing sample from a process stream enters valve 1 through tubing 33a, passes across the diaphragm to the port for tubing 33b, out of the valve into sample loop 101, returns into the valve through the port for tubing 33e, passing across the diaphragm and through the port for tubing 33f to vent. At the same time, a continuously flowing carrier gas, typically helium, is entering the port for tubing 33d passing across the diaphragm, exiting the valve through the port for tubing 33c, passing through a separation column and then to a detector. In this mode the flow paths between the ports for tubings 33b and 33c, 33d and 33e and 33f and 33a are closed to flow therebetween.

Simultaneously, in the outer circle of ports a continuously flowing sample from a process stream enters valve 1 at the port for tubing 33g, passes across the diaphragm to the port for tubing 33h, out of the valve into sample loop 103, returns into the valve through the port for tubing 33k, passing across the diaphragm and through the port for tubing 33l to vent. At the same time, a continuously flowing carrier gas, typically helium, is entering the port for tubing 33j passing across the diaphragm, exiting the valve through the port for tubing 33i passing through a separation column and then to a detector. In this mode the flow paths between the ports for tubings 33h and 33i, 33j and 33k and 33l and 33g are closed to flow therebetween.

An electrical pulse mechanically switches the position of the valve. In the switching operation the plungers that have sealed the diaphragm 23 against the flat surface of the valve cap face 27 remain in sealed position while the rotation of the detent plate 15 causes the spherical bodies that have been resting in the indentations in the detent plate to be moved out of the indentations to ride on the surface of the detent plate thereby providing pressure against their plungers that cause these plungers to press against the diaphragm with force sufficient to seal the diaphragm to the flat surface of the valve cap face 27. There is a switching period measured in milliseconds, typically 12 to 15, in which all flow paths between ports are simultaneously closed. The switching of positions of this valve is accomplished so rapidly and smoothly that analytical detection devices, which normally experience a surge with the change of sampling positions using previously known valves, do not detect position change except by change of composition analysis.

The rotation of the detent plate is stopped to align the indentations on the detent plate with the spherical bodies that in the preceding mode were the link in transmitting the pressure from the detent plate to seal the diaphragm against the flat surface of the valve cap face 27. This causes these spherical bodies to rest in the indentations thereby allowing the fluid pressure at the ports to move the diaphragm into the grooves breaking the seal thereby opening a passage between ports. The spherical bodies that are not aligned with indentations maintain the pressure that seals the diaphragm to the flat surface of the valve cap face 27 thereby providing flow paths through the valve which are alternative to those in the previous mode.

In mode II, as indicated in FIG. 5, in the inner circle of ports a continuously flowing sample from a process stream now enters valve 1 at the port for tubing 33*a*, passes across the diaphragm and through the port for tubing 33*f* to vent purging the portion of the inner passageway between the port for tubing 33*a* and the port for tubing 33*f* of the previous sample. At the same time, a continuously flowing carrier gas, typically helium, is entering the port for tubing hd passing across the diaphragm, exiting the valve through the port for tubing 33*e* passing through the sample loop 101, back into the valve at the port for tubing 33*b*, across the diaphragm and out the port for tubing 33*c* to inject a sample into a detector. In this mode the-flow paths between the port for tubings 33*c* and 33*d*, 33*e* and 33*f* and 33*a* and 33*b* are closed to flow therebetween.

Simultaneously, in the outer circle of tubings a continuously flowing sample from a process stream enters valve 1 at the port for tubing 33*g*, passes across the diaphragm and through the port for tubing 33*l* to vent purging the portion of the inner passageway between the port for tubing 33*g* and the port for tubing 33*l* of the previous sample. At the same time, a continuously flowing carrier gas, typically helium, is entering the port for tubing 33*j* passing across the diaphragm, exiting the valve through the port for tubing 33*k* to pass through sample loop 103 back into the valve at the port for tubing 33*h*, across the diaphragm and out of the valve at the port for tubing 33*i* to inject a sample into a separation column and thence to a detector. In this mode the flow paths between the ports for tubings 33*g* and 33*h*, 33*i* and 33*j* and 33*k* and 33*l* are closed to flow therebetween.

The electrical pulse is again activated to advance the rotation of the detent plate to the next position and again align the flow paths in the conformation of Mode I. At the opening of the flow paths of Mode I any sample material trapped between the port for tubing 33*g* and the port for tubing 33*l* or the port for tubing 33*a* and the port for tubing 33*f* is the immediate last material passing therethrough before the change of flow path and is, therefore, like the material now passing to the sample loops.

The invention thus being described, it will be obvious that the same may be varied in many ways. Such variations are not to be regarded as a departure from the spirit and scope of the invention and all such modifications are intended to be included within the scope of the following claims.

What is claimed is:

1. A multiport valve comprising (A) a plunger body having a first, flat face and a second, flat face, (B) a detent plate; (C) a flat surface abutting the first, flat face of the plunger body; (D) at least one diaphragm inserted between the first, flat face of the plunger body and the flat surface abutting the first, flat face of the plunger body covering the area therebetween; (E) a multiplicity of plungers and (F) a multiplicity of spherical bodies wherein:

(1) the first, flat face of the plunger body comprises at least two circular grooves with the grooves pierced at equal intervals by a multiplicity of cylindrical, plunger passages with each, plunger passage (a) passing through the plunger body to the opposing, second, flat face, (b) retaining therein a plunger and (c) retaining partially therein a spherical body;

(2) the surface abutting the grooved, first, flat face of the plunger body includes transport tubing openings aligned at equal intervals in at least two circular patterns concentric with and having the same diameter as a circular groove of the plunger body and with openings aligned between the plunger passages of the plunger body; and (3) the detent plate (a) comprises a flat face having indentions, half the number as the number of transport tube openings, therein aligned at equal intervals in at least two circular patterns concentric with and having the same diameter as the circular grooves; (b) is held in position with the flat face of the detent plate facing the second, flat face of the plunger body so that the flat face of the detent plate holds each spherical body in sufficient, rollable tension in a retaining, plunger passage against a plunger to seal the diaphragm at the opposing end of the plunger against the surface abutting the grooved, first, flat face of the plunger body; and (c) is rotatable around an axis designated by a line joining the centers of the circles described by the two circular grooves and the circular patterns of indentations so that on partial rotation of the detent plate, the spherical bodies providing tension on a portion of the plungers in the same groove simultaneously come to rest in indentations thereby allowing relaxation of the sealing of the diaphragm by this portion of the plungers against the abutting surface.

2. A multiport valve of claim 1 wherein the at least one diaphragm covering the area between (1) the first, flat face of the plunger body and (2) the surface abutting the first, flat face of the plunger body is sufficiently resilient to be displaced into groove by pressure of fluid issuing from a transport tubing opening.

3. A multiport valve of claim 2 wherein the at least one diaphragm comprises a first diaphragm of heat resistant plastic film and a second diaphragm of synthetic fiber fabric.

4. A multiport valve of claim 3 wherein a valve cap attachable to the plunger body at the first, flat face of the plunger body comprises (1) a valve cap body, (2) the surface abutting the first, flat face of the plunger body and (3) a multiplicity of transport tubings press fitted into and through the valve cap body and machine lapped to the surface abutting the first, flat face of the plunger body forming thereby means of entrance and exit for fluid.

5. A multiport valve of claim 4 comprising means attached to the detent plate providing controlled, rotational motion to the detent plate.

6. A multiport valve of claim 5 further comprising a spring nest positioned to maintain compressive tension of the detent plate against the spherical bodies.

7. A multiport valve of claim 6 further comprising a casing surrounding the spring nest.

8. A multiport valve of claim 6 wherein the spring nest comprises a spring washer.

9. A multiport valve of claim 7 wherein the spring nest comprises a spring washer.

10. A multiport valve of claim 9 wherein means attached to the detent plate providing controlled, rotational motion to the detent plate is a rotary, electric solenoid.

11. A multiport valve of claim 9 wherein there are (a) twelve transport tubing openings in the valve cap; (b) the first, flat face of the plunger body has two, circular grooves each pierced by six cylindrical, plunger passages and (c) the flat face of the detent plate has six indentions therein aligned in two, circular patterns concentric with and having the same diameter as the two, circular grooves of the plunger body.

12. A multiport valve of claim 11 wherein means attached to the detent plate providing controlled, rotational motion to the detent plate is a rotary, electric solenoid.

13. A multiport valve comprising (A) a plunger body having a first, flat face and a second, flat face, (B) a detent plate; (C) a valve cap attachable to the plunger body at the first, flat face of the plunger body comprising a surface abutting the first, flat face of the plunger body and a multiplicity of transport tubings press fitted into and through the valve cap body and machine lapped to the surface abutting the first, flat face of the plunger body forming thereby means of entrance and exit for fluid; (D) at least one diaphragm comprising a first diaphragm of heat resistant plastic film and a second diaphragm of synthetic fiber fabric inserted between the first, flat face of the plunger body and the surface abutting the first, flat face of the plunger body covering the area therebetween; (E) a casing surrounding a spring nest positioned to maintain compressive tension of the detent plate against the spherical bodies; (F) a means attached to the detent plate providing controlled, rotational motion to the detent plate; (G) a multiplicity of plungers and (H) a multiplicity of spherical bodies wherein:

(1) the first, flat face of the plunger body comprises at least two circular grooves with the grooves pierced at equal intervals by a multiplicity of cylindrical, plunger passages with each, plunger passage (a) passing through the plunger body to the opposing, second, flat face, (b) retaining therein a plunger and (c) retaining partially therein a spherical body;

(2) the surface abutting the grooved, first, flat face of the plunger body includes transport tubing openings aligned at equal intervals in at least two circular patterns each concentric with and having the same diameter as a circular groove of the plunger body and with openings aligned between the plunger passages of the plunger body; and (3) the detent plate (a) comprises a flat face having indentions therein aligned at equal intervals in at least two circular, indentation patterns each concentric with and having the same diameter as a circular groove; (b) is held in position with the flat face of the detent plate facing the second, flat face of the plunger body so that the flat face of the detent plate holds each spherical body in sufficient, rollable tension in a retaining, plunger passage against a plunger to seal the diaphragm at the opposing end of the plunger against the surface abutting the grooved, first, flat face of the plunger body; and (c) is rotatable around an axis designated by a line joining the centers of the circles described by the circular grooves and the circular, indentation patterns so that on partial rotation of the detent plate, the spherical bodies providing tension on the portion of the plungers in the same groove simultaneously come to rest in indentations thereby allowing relaxation of the seal of the diaphragm by these plungers against the abutting surface so that the resilient diaphragm is displaced into a groove by pressure of fluid that issues from a transport tubing opening.

14. A multiport valve of claim 13 wherein means attached to the detent plate providing controlled, rotational motion to the detent plate is a rotary, electric solenoid.

15. A multiport valve comprising (A) a plunger body having a first, flat face and a second, flat face, (B) a detent plate; (C) a valve cap attachable to the plunger body at the first, flat face of the plunger body comprising a surface abutting the first, flat face of the plunger body and twelve transport tubings press fitted into and through the valve cap body and machine lapped to the surface abutting the first, flat face of the plunger body forming thereby means of entrance and exit for fluid; (D) a diaphragm comprising a first diaphragm of heat resistant plastic film and a second diaphragm of synthetic fiber fabric inserted between the first, flat face of the plunger body and the surface abutting the first, flat face of the plunger body covering the area therebetween; (E) a casing surrounding a spring nest positioned to maintain compressive tension of the detent plate against the spherical bodies and (F) a means attached to the detent plate providing controlled, rotational motion to the detent plate wherein:

(1) the first, flat face of the plunger body comprises two, circular grooves with the grooves pierced at intervals by six cylindrical, plunger passages with each, plunger passage (a) passing through the plunger body to the opposing, second, flat face, (b) retaining therein a plunger and (c) retaining partially therein a spherical body;

(2) the surface abutting the grooved, first, flat face of the plunger body includes twelve transport tubing openings aligned at intervals in two, circular patterns of six openings, each pattern concentric with and having the same diameter as a circular groove of the plunger body and with openings aligned between the plunger passages of the plunger body; and (3) the detent plate (a) comprises a flat face having indentions therein aligned at intervals in two circular, indentation patterns each concentric with and having the same diameter as a circular groove; (b) is held in position with the flat face of the detent plate facing the second, flat face of the plunger body so that the flat face of the detent plate holds each spherical body in sufficient, rollable tension in a retaining, plunger passage against a plunger to seal the diaphragm at the opposing end of the plunger against the surface abutting the grooved, first, flat face of the plunger body; and (c) is rotatable around an axis designated by a line joining the centers of the circles described by the two, circular grooves and the two, circular, indentation patterns so that on partial rotation of the detent plate, the spherical bodies providing tension on a portion of the plungers in the same groove simultaneously come to rest in indentations thereby allowing relaxation of the sealing of the diaphragm by these plungers against the abutting surface so that the resilient diaphragm is displaced into a groove by pressure of fluid that issues from a transport tubing opening.

16. A multiport valve of claim 15 wherein means attached to the detent plate providing controlled, rotational motion to the detent plate is a rotary, electric solenoid.

17. In a multiport valve comprising:

(A) an even number of ports spaced equidistantly on at least two channels each arranged in a circular configuration and having (B) identical blocking means for mechanically blocking flow wherein the blocking means are equally spaced between each of the openings, comprising (1) a plunger-retaining passage, perpendicular to and opening into the channel beneath a flexible diaphragm with (2) a plunger retained in the plunger-retaining passage so that one end of the plunger (a) presses the diaphragm into sealing arrangement in the channels and (b) the other end of the plunger compressively abuts (3) a spherical body partially retained in the plunger-retaining passage in rollable, compressed contact with a flat surface of (C) a detent plate containing indentations on the flat surface with the indentations being half in number as the number of the ports and each equidistantly arranged in a circular configuration concentric with and having the same diameter as the midpoint of a channel;

an apparatus for switching flow paths between adjacent ports comprising a means for rotating the detent plate to a position allowing every other spherical body of a circular configuration to come to rest in an indentation for a controlled period of time and subsequently, sequentially rotating the detent plate to a position at which an adjacent spherical body in the circular configuration comes to rest in an indentation for a controlled period of time.

18. A multiport valve of claim 17 wherein means for rotating the detent plate is a rotary, electric solenoid.

19. Using a multiport valve comprising:

(A) an even number of ports spaced equidistantly on at least two channels arranged in circular configuration and having (B) identical blocking means for mechanically blocking flow wherein the blocking means are equally spaced between each of the tubings and comprise (1) a plunger-retaining passage, perpendicular to and opening into the channel beneath a flexible diaphragm with (2) a plunger retained in the plunger-retaining passage so that one end of the plunger (a) presses the diaphragm into sealing arrangement in a channel and (b) the other end of the plunger compressively abuts (3) a spherical body partially retained in the plunger-retaining passage in rollable, compressed contact with a flat surface of (D) a detent plate containing indentations on the flat surface with the indentations being half in number as the number of ports and equidistantly arranged in at least two circular configurations each concentric with and having the same diameter as the midpoint of a channel;

a method for switching flow paths between adjacent ports the method comprising rotating the detent plate to a position at which every other spherical body of a circular configuration comes to rest in an indentation for a controlled period of time and subsequently, sequentially rotating the detent plate to a position at which an adjacent spherical body in the same circular configuration comes to rest in an indentation for a controlled period of time.

* * * * *